United States Patent
Subramanyam

(10) Patent No.: US 7,922,975 B2
(45) Date of Patent: Apr. 12, 2011

(54) RESONANT SENSOR CAPABLE OF WIRELESS INTERROGATION

(75) Inventor: Guru Subramanyam, Dayton, OH (US)

(73) Assignee: University of Dayton, Dayton, OH (US)

( * ) Notice: Subject to any disclaimer, the term of this patent is extended or adjusted under 35 U.S.C. 154(b) by 284 days.

(21) Appl. No.: 12/172,330

(22) Filed: Jul. 14, 2008

(65) Prior Publication Data

US 2010/0008825 A1    Jan. 14, 2010

(51) Int. Cl.
*G01N 27/00* (2006.01)
(52) U.S. Cl. ................................ 422/82.01
(58) Field of Classification Search ............ 422/58, 422/82.01
See application file for complete search history.

(56) References Cited

U.S. PATENT DOCUMENTS

| | | | |
|---|---|---|---|
| 5,640,042 A | 6/1997 | Koscica et al. | |
| 5,689,275 A | 11/1997 | Moore et al. | |
| 6,377,440 B1 | 4/2002 | Zhu et al. | |
| 6,404,614 B1 | 6/2002 | Zhu et al. | |
| 6,433,375 B1 | 8/2002 | Carlsson et al. | |
| 6,454,914 B1 | 9/2002 | Nakamura | |
| 6,525,630 B1 | 2/2003 | Zhu et al. | |
| 7,030,463 B1 | 4/2006 | Subramanyam et al. | |
| 2002/0158717 A1 | 10/2002 | Toncich | |
| 2002/0163400 A1 | 11/2002 | Toncich | |
| 2003/0001692 A1 | 1/2003 | Chiu et al. | |
| 2003/0020567 A1 | 1/2003 | Chappell et al. | |
| 2003/0040004 A1 | 2/2003 | Hefti et al. | |
| 2007/0024400 A1 | 2/2007 | Subramanyam et al. | |
| 2007/0069264 A1* | 3/2007 | Subramanyam et al. | 257/295 |
| 2007/0176217 A1 | 8/2007 | Subramanyam et al. | |

FOREIGN PATENT DOCUMENTS

| | | |
|---|---|---|
| JP | 6-75256 A | 3/1994 |
| WO | 02 084310 A1 | 10/2002 |
| WO | 02 084685 A1 | 10/2002 |
| WO | 2006/104902 A1 | 10/2006 |

OTHER PUBLICATIONS

Tkac, J.; Whittaker, J.W.; Ruzgas, T. "The use of single walled carbon nanotubes dispersed in a chitosan matrix for preparation of a galactose biosensor." Biosensors and Bioelectronics, 2007, 22, pp. 1820-1824.*

Yoon et al "Passive wireless sensors using electrical transition of carbon nanotube junctions in polymer matrix" Smart Materials and Structures, vol. 15, Dec. 13, 2005, pp. S14-S20.

International Search Report and Written Opinion dated Dec. 4, 2009 pertaining to International application No. PCT/US2009/050512.

* cited by examiner

*Primary Examiner* — Walter D Griffin
*Assistant Examiner* — Bobby Ramdhanie
(74) *Attorney, Agent, or Firm* — Dinsmore & Shohl, LLP

(57) ABSTRACT

A resonant sensor for detecting a specific environmental analyte is presented. The resonant sensor comprises a top conductive layer of two ground conductors and a center signal line, a bottom conductive layer of two ground lines shunted together by a shunt line and a sensing layer positioned between the top conductive layer and the bottom conductive layer. A capacitor is created by the overlap of the center signal line of the top conductive layer and the shunt line of the bottom conductive layer. Electrical properties of the sensing layer change in response to binding the specific environmental analyte with the sensing layer. The sensing layer can be an electro-optic polymer. Nanoparticles or carbon nanotubes can be dispersed within the sensing layer to bind with the specific environmental analyte. An integrated antenna can be incorporated into to sensor to receive radio frequencies for wireless, passive sensing.

17 Claims, 8 Drawing Sheets

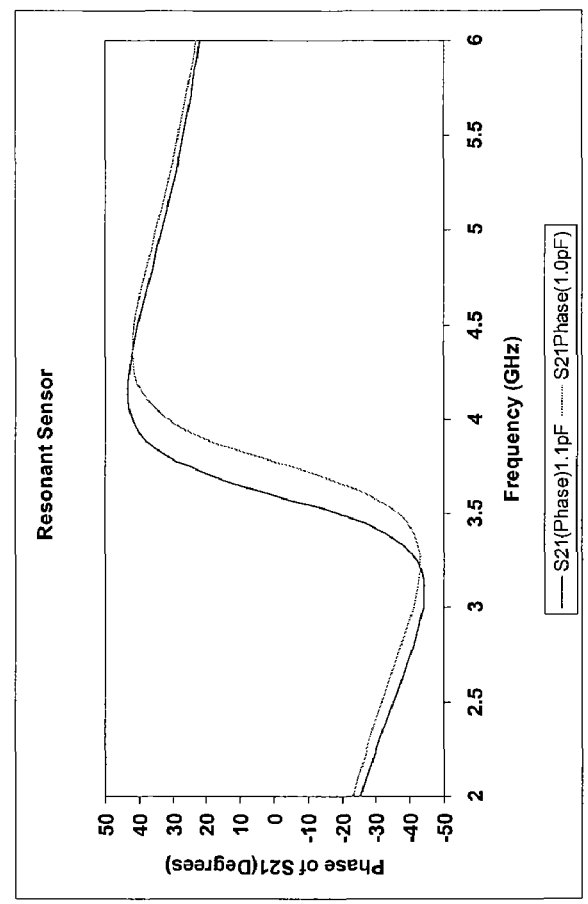
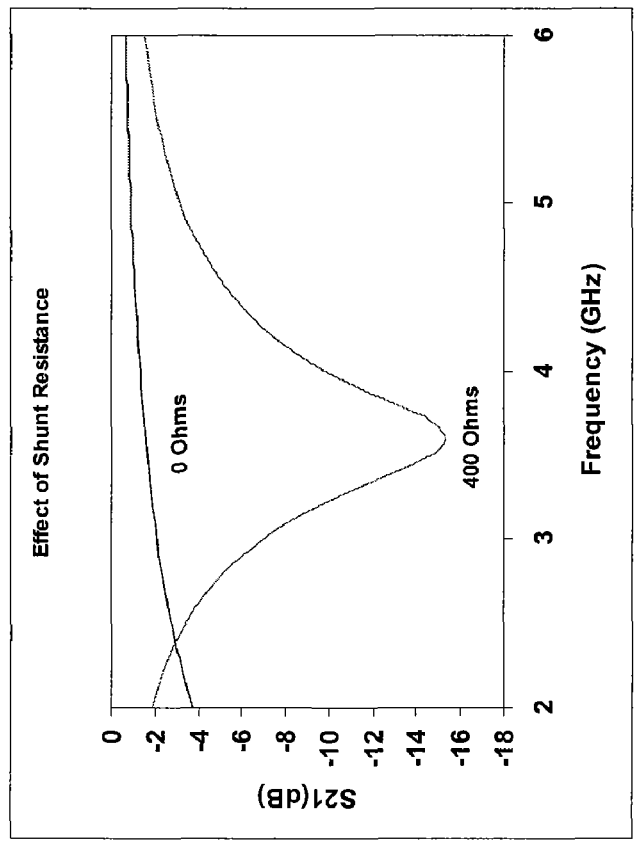
Figure 6
Figure 5

RESONANT SENSOR CAPABLE OF WIRELESS INTERROGATION

BACKGROUND OF THE INVENTION

The application generally relates to a resonant sensor and, in particular, relates to a resonant bio-chemical polymer sensor capable of wireless, passive sensing interrogation.

Resonant sensors are sensors whose output can vary with respect to changes in specific environment conditions present near the resonant sensor. Typically, resonant sensors are comprised of an inductance-capacitance (LC) circuit with a specific resonance frequency.

Polymers that are biopolymers, such as, for example Deoxyribonucleic acid (DNA) cetyltrimethylammonium (CTMA) and bovine serum albumin (BSA) have been found to have unique dielectrical properties. These biodielectrics can exhibit voltage tunable dielectric properties at room temperatures at microwave frequencies. Dielectric tunability of more than 50% has been measured in DNA-CTMA biopolymer and about 40% in BSA-polyvinyl alcohol (PVA) polymer. Therefore, the voltage dependent dielectric tunability of these polymers can offer a unique opportunity to use the polymers in resonant sensor applications.

Therefore, there is a need for a sensor that is resonant and that is applicable for sensing biochemicals, or other trace chemicals, in solid or gaseous form using a functionalized biopolymer as a sensing layer.

There is also a need for a sensor that is resonant for wireless passive sensing by combining radio frequency (RF) and electro-optic measurement techniques with a polymer resonant sensor that is applicable for sensing biochemicals, trace chemicals in solid or gaseous form.

BRIEF SUMMARY OF THE INVENTION

It is against the above background that in one embodiment, a resonant sensor for detecting a specific environmental analyte is presented. The sensor can be comprised of a top conductive layer of two ground conductors and a center signal line, a bottom conductive layer of two ground lines shunted together by an inductive shunt line and a sensing layer positioned between the top conductive layer and the bottom conductive layer. The top conductive layer can have perforations to allow the specific environmental analyte to interact with the sensing layer. The sensor can be fabricated on any substrate including silicon, sapphire, alumina, plastic, glass or any other suitable material. In another embodiment, a capacitor can be created by the overlap of the center signal line of the top conductive layer and the inductive shunt line of the bottom conductive layer. The capacitor and shunt line may be used to form a resonant circuit with a specific resonance frequency. With the above sensor, electrical properties of the sensing layer will change in response to the specific environmental analyte binding with the sensing layer. In yet another embodiment, the sensing layer can be an electro-optic biopolymer. In still another embodiment, the sensing layer can be a piezoelectric thin film. In still yet another embodiment, an antenna can be integrated into the sensor to receive and send radio frequencies.

In accordance with another embodiment, radio frequency and electric optical measurement techniques are combined to provide increased sensor selectivity and sensitivity.

In accordance with another embodiment, the electric-optical polymer sensing layer can contain dispersed nanoparticles or carbon nanotubes to enhance specificity and selectivity to an analyte.

In accordance with still another embodiment, the polymer sensing layer can contain organic and inorganic composite materials.

In accordance with yet another embodiment, the sensor can be interrogated in a wireless fashion for passive sensing.

Accordingly, it is a feature of the embodiments to provide a highly sensitive and highly selective sensor that can be a resonant sensor and that can be applicable for sensing specific environment conditions, such as, for example, biochemicals, trace chemicals in solid or gaseous form. Still other features and advantages of the embodiments will be apparent in light of the description embodied herein.

BRIEF DESCRIPTION OF THE SEVERAL VIEWS OF THE DRAWINGS

The following detailed description of specific embodiments can be best understood when read in conjunction with the following drawings, where like structure is indicated with like reference numerals and in which:

FIG. 5 graphs the effect of change in shunt resistance when the shunt resistance goes to zero ohms (a complete short) according to an embodiment of the present application.

FIG. 6 graphs the effect of change in capacitance by 10% on the phase of the scattering parameter S21 according to an embodiment of the present application.

DETAILED DESCRIPTION

In the following detailed description of the embodiments, reference is made to the accompanying drawings that form a part hereof, and in which are shown by way of illustration, and not by way of limitation, specific embodiments in which the invention may be practiced. It is to be understood that other embodiments may be utilized and that logical, mechanical and electrical changes may be made without departing from the spirit and scope of the present invention.

Figure 1B:
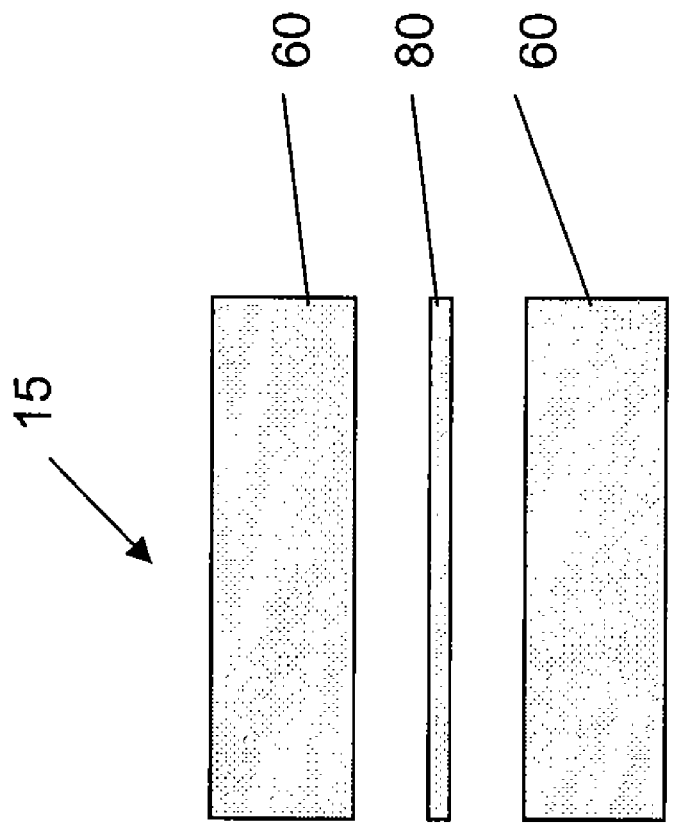
FIG. 1b illustrates the top conductive layer of the resonant sensor according to an embodiment of the present application.
Figure 1A:
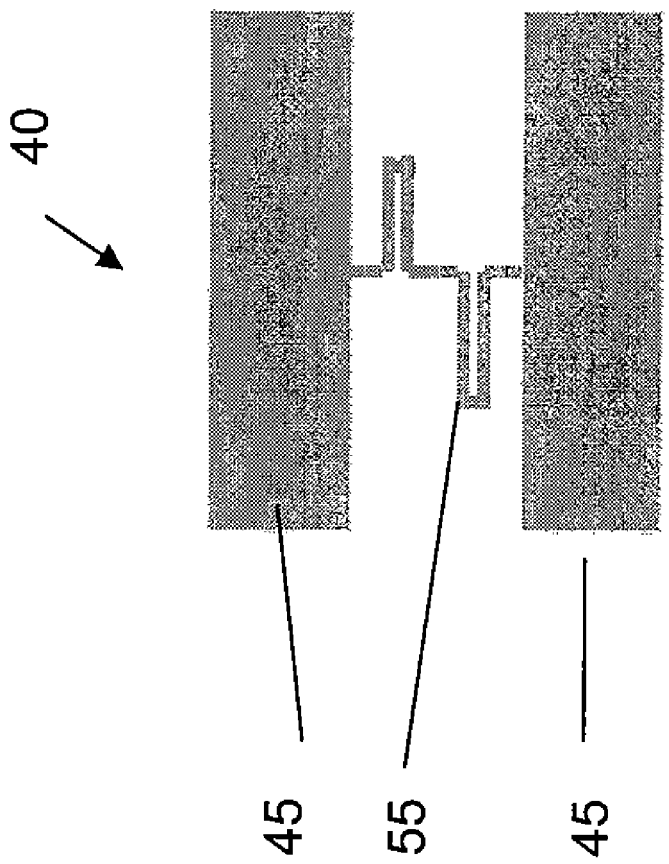
FIG. 1a illustrates the bottom conductive layer of the resonant sensor according to an embodiment of the present application.

Referring initially to FIGS. 1a-d, an resonant sensor 10 (best shown by FIG. 1c) is illustrated. In FIG. 1a, a patterned bottom conductive layer 40 is illustrated. In one embodiment, the bottom conductive layer 40 can be comprised of platinum, gold or any other suitable metal. In another embodiment, the bottom conductive layer 40 can be comprised of a conducting polymer. The bottom conductive layer 40 can be comprise of two ground lines 45 shunted together by a conductor, or shunt line 55. The shunt line 55 can be patterned in a non-linear pattern to add inductance to the shunt line 55 as illustrated in FIG. 1a.

FIG. 1b illustrates the top conductive layer 15 with its Ground-Signal-Ground (GSG) coplanar waveguide (CPW) transmission line pattern. In one embodiment, the top conductive layer 15 may be comprised of gold, platinum, combinations of gold and platinum, or any other suitable metal. In another embodiment, the top conductive layer 15 can be comprised of a conducting polymer. The top conductive layer 15 can be comprised of a central signal strip 80 positioned between two ground conductors 60 of the CPW transmission line. In one embodiment, the top conductive layer 15 can be perforated.

In one embodiment, both the bottom conductive layer 40 and the top conductive layer 15 can be comprised of metal. In another embodiment, both the bottom conductive layer 40 and the top conductive layer 15 can be comprised of conducting polymers. In still another embodiment, one of the bottom conductive layer 40 and the top conductive layer 15 can be comprised of a metal and the other layer can be comprised of a conducting polymer.

Figure 1C:
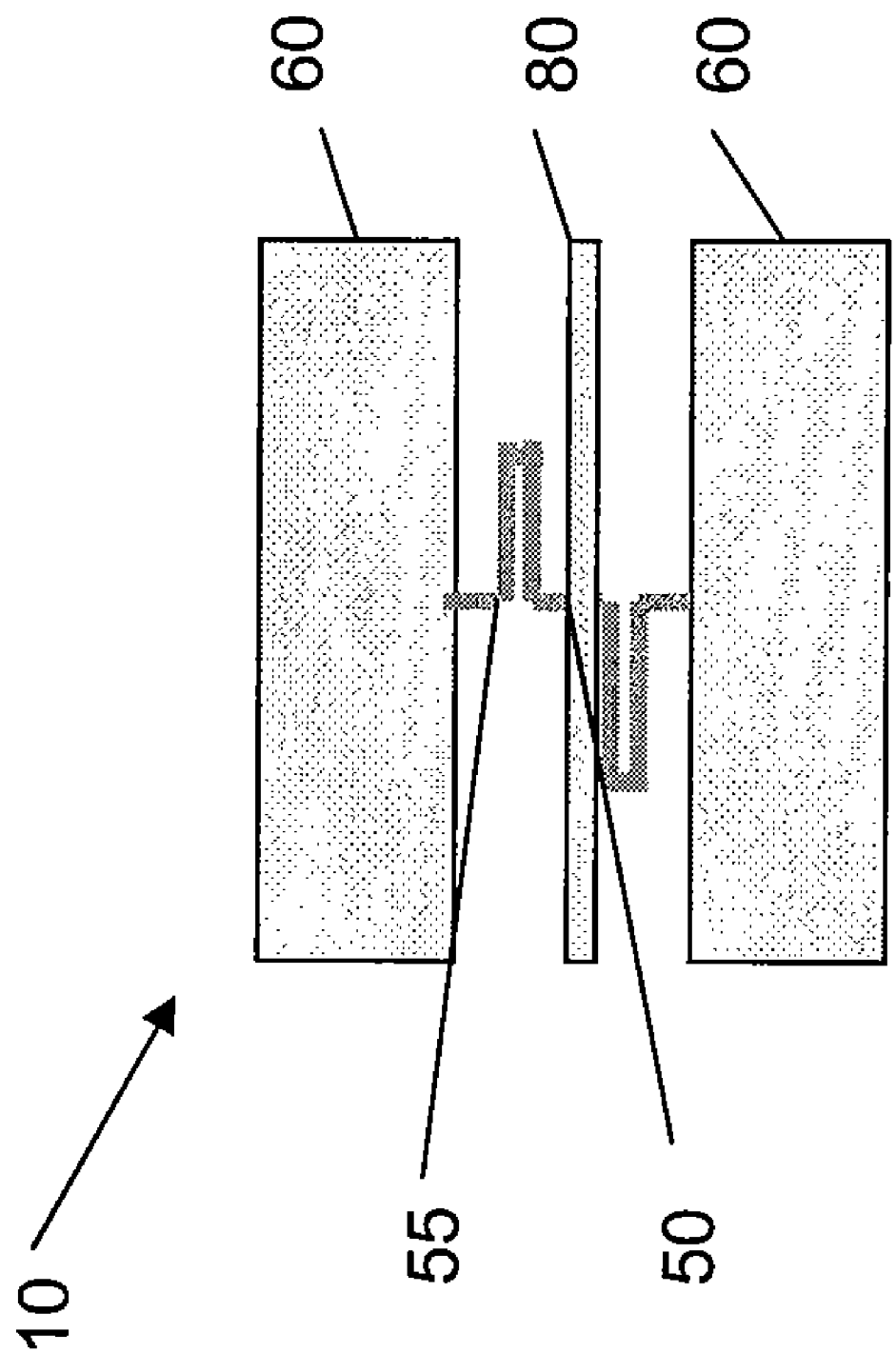
FIG. 1c illustrates a top view of the resonant sensor according to an embodiment of the present application.

Referring to FIG. 1c, a top view of the resonant sensor 10 is illustrated. The overlap area 50 between the top conductive layer 15 and the bottom conductive layer 40 can form the capacitor region. The two ground conductors 60 of the top conductive layer 15 can lie directly above the ground lines 45 of the bottom conductive layer 40. The central signal strip 80 can be centered between the ground conductors 60 and can be perpendicular to the shunt line 55 of the bottom conductive layer 40. The active region 55 of the test structure capacitance device can be defined by the overlap area of the center signal strip 80 of the top conductive layer 15 and the shunt line 55 in the bottom conductive layer 40. The active region 50 can contain the capacitor loading. The test structure capacitance device can have a large ground pad capacitor that results from the overlap of the ground lines 45 of the bottom conductive layer 40 and the ground conductors 60 of the top conductive layer 15. The ground line conductors 45 in the bottom conductive layer 40 and the ground conductors 60 of the top conductive layer 15 can be effectively shorted at the frequencies of interest, due to the large capacitance between the two layers. A polymer sensing layer (not shown) can be positioned between the top conductive layer 15 and the bottom conductive layer 40. In one embodiment, perforations in the top conductive layer 15 can provide access for the specific environmental analytes to interact with the polymer sensing layer.

The coplanar waveguide based device can be comprised of coplanar waveguide transmission lines at the input 30 and output 20, shunt loaded by a series LC, or resonant, circuit in the middle. The LC circuit can comprise of an inductor, represented by the letter L, and a capacitor, represented by the letter C. In other words, the test capacitor area 50 and the inductive shunt line 55 in the bottom conductive layer 40 can form a resonant circuit with a specific resonance frequency. The LC resonant circuit can act as a shunt resonator, as the series LC circuit can be terminated in a virtual short circuit to ground, due to the large ground pad capacitor in the device. When the polymer sensing layer binds the environmental analytes, either a capacitance change or a leakage conductance change between the top conductive layer 15 and the bottom conductive layer 25 or between the signal line and ground line can occur. When this change occurs, the ratio of output power to input power changes. Additionally, the reflected power (S11 in dB) as well as the phase angle between input and output (Phase of S21 in Degrees) can also change. Capacitance change can also result in a resonance frequency shift. Measuring a multitude of different electrical parameters can result in improved specificity and a decrease in false positives.

Figure 1D:
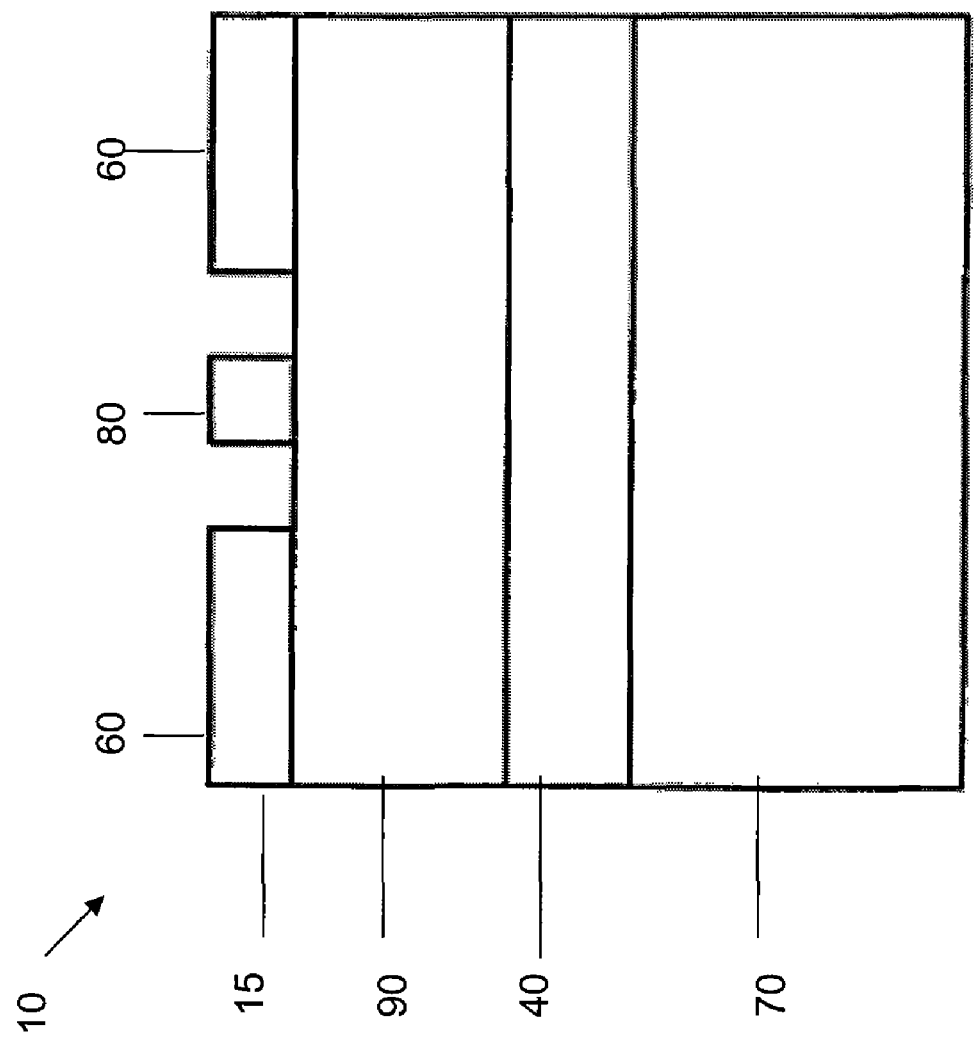
FIG. 1d illustrates a cross-sectional view of the resonant sensor according to an embodiment of the present application.

FIG. 1d represents a cross-sectional view of the sensor. In the embodiment of this figure, the two conductive layers: the top 15 and the bottom 40 are shown. The top conductive layer 15 can comprise the GSG CPW transmission line. As discussed above, the overlap area of the signal line and the bottom conductive layer 40 can define the test capacitor 50. In one embodiment, the resonant sensor 10 can be designed on the CPW transmission line that has a multilayer structure fabricated on a substrate 70. In one embodiment, the patterned bottom conductive layer 40 can be processed on a substrate 70 comprised of a wafer of high resistivity silicon. Alternatively, the substrate 70 can be comprised of sapphire, alumina, plastic, glass or any other suitable material. The bottom conductive layer 40 can be covered by a sensing layer 90.

In one embodiment, the polymer sensing layer 90 can be comprised of any polymer and can be, for example, a biopolymer. In one embodiment, the biopolymer can be an electrooptical (EO) polymer such as, for example, DNA-based polymers or any other EO polymer, such as, for example, DNA-CTMA and BSA. Using a biopolymer with specific EO transmittance and/or absorption properties at the wavelength of the light beam used, it can be determined whether a specific analyte had been captured by measuring the change in the absorption/transmission characteristics of the polymer.

In another embodiment, nanoparticles, such as, for example, metals, dielectrics, biomolecules, can be dispersed in the polymer sensing layer 90 to enhance specificity and selectivity to an analyte. The embedded nanoparticles can specifically bind with the environmental analytes of interest. In one embodiment, the nanoparticles can be gold that can be specifically designed to sense chemical and biological analytes by binding with those analytes. Alternatively, carbon nanotubes can be dispersed in the polymer sensing layer 90 to enhance specificity and selectivity to an analyte. In still another embodiment, organic and inorganic composite materials can also be mixed into the polymer sensing layer 90 to enhance specificity and selectivity to an analyte.

In yet another embodiment, the polymer in the polymer sensing layer 90 can be replaced with a multi-layered structure (for example, a three layer optical waveguide, i.e., clad/core/clad) which then can be used as the sensing layer 90. In still yet another embodiment, the polymer in the polymer sensing layer 90 can be replaced with a piezoelectric thin film.

Finally, a top conductive electrode 15 can be deposited on top of the sensing layer 90 and can be patterned to form a CPW transmission line.

Figure 2:
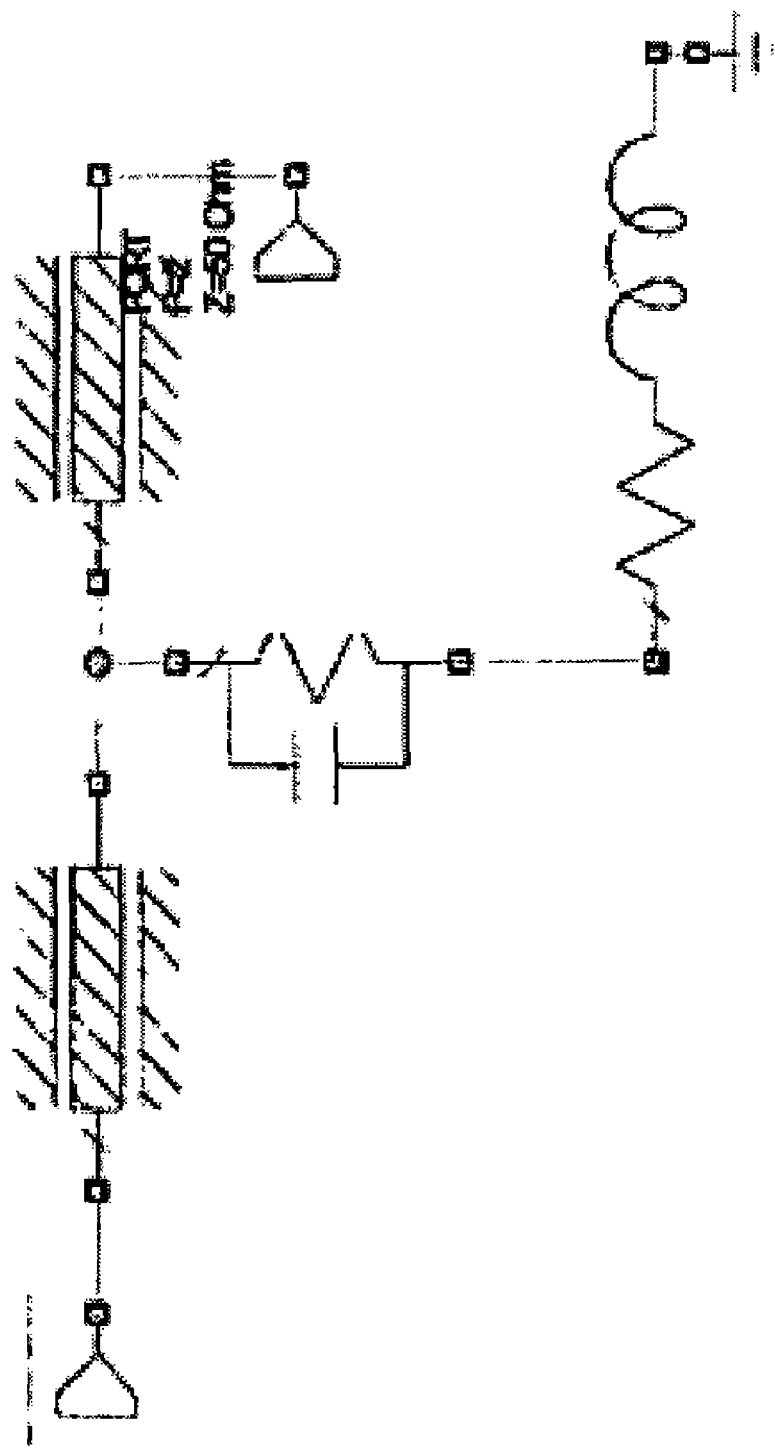
FIG. 2 illustrates an equivalent circuit of the resonant sensor according to an embodiment of the present application.

The equivalent circuit of the resonant sensor showing the shunt LC resonance circuit is illustrated in FIG. 2. The electrical circuit shows the input and output feed lines, the LC resonator shunting the line in the middle. The shunt resistor across the test capacitor can model the leakage conductance of the polymer sensing layer 90. The inductor can be modeled with a parasitic resistor in series. The values shown can be example values for a resonant sensor designed for resonance close to about 3.75 GHz. The resonant sensor can be designed for any frequency, including the FCC approved Industrial, Scientific and Medical (ISM) band, such as, for example 2.45 GHz or for low MHz.

The tailored bipolymers can be used as the sensing layer 90 for specific environment analytes, such as biochemicals or chemicals, which can allow for highly sensitive resonance sensors with the potential for high selectivity and high sensitivity. The parameters that can be affected by the specific environmental condition, or analyte, can be: 1) the capacitance of the test capacitor in the shunt resonator, and 2) shunt resistance of the capacitor modeling in the leakage conductance of the test capacitor.

The resonant sensor can be modeled using Applied Wave Research, Inc. (AWR) Microwave Office software tools. In one embodiment, a network analyzer and an on-wafer microwave probe station can be used to measure the scattering parameters (S parameters) of the resonant test structure. The setup that can be used to measure the S parameters can be a two-port network, with one port at each end of the signal line 80 of the top conductive layer 15. A two-port network can yield a 2×2 matrix of S parameters that can relate the reflected waves (or voltages) to the incident waves (or voltages). The procedure for the experimental determination of S parameters can use the following steps. First, the network analyzer and probe station can be calibrated to the device over the frequency range of interest (1-20 GHz) using a Line-Reflect-Reflect-Match (LRRM) calibration as known in the art. Then, the DC bias voltage can be applied to the signal lead of the probe (when applicable). Finally, the S parameters can be recorded and saved. The S parameter measurements can be performed before and after exposure to a specific analyte in a controlled environment. These measurements can help determine the exact values in the electrical model of the resonant test structure.

Additionally, the measured S parameters can be then imported into the AWR Microwave Office simulation package or a Microsoft Excel worksheet. The capacitance C(V) can be obtained by the standard parallel plate capacitance calculation, with the dielectric permittivity of the polymer in the polymer sensing layer 90, and the overlap area 50 of the center signal strip 80 and the shunt line 55. The device capacitance C(V) can be given by:

$$C(V) = \epsilon_0 \cdot \epsilon_r \cdot A / t_p \quad (1)$$

where $\epsilon_0$ is the dielectric permittivity of free space, $\epsilon_r$ is the dielectric permittivity of the polymer in the polymer sensing layer 90, A is the area of overlap 50 of the top center signal strip 80 and the shunt conductor 55 within the capacitive test structure, and $t_p$ is the thickness of the polymer in the polymer sensing layer 90.

The inductance (L) of the line can be calculated using Equation 2:

$$L = (Z_0/(2\pi f)) \sin(2\pi l / \lambda_g) \quad (2)$$

where, $Z_0$ is the characteristic impedance of the CPW transmission line, f is the operating frequency, and $\lambda_g$ is the guide-wavelength.

The shunt resistance (R(V)) of the test structure can be calculated using Equation 3:

$$R(V) = 1/(\omega C(V) \tan \delta) \quad (3)$$

where, C(V) is the capacitance at a single bias voltage, $\omega$ is the angular frequency and $\tan \delta$ is the loss-tangent of the polymer in the polymer sensing layer 90.

Figure 4:
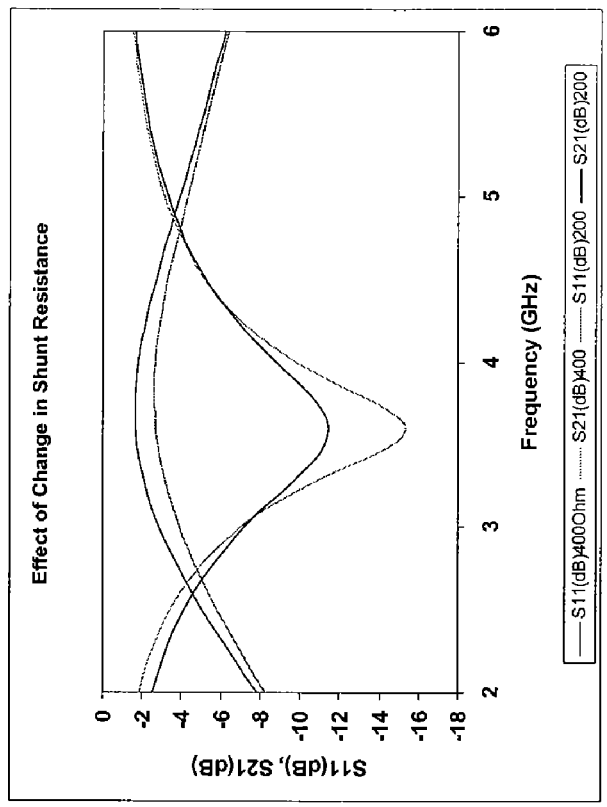
FIG. 4 graphs the effect of change in shunt resistance (effective AC resistance between the signal conductor and the ground conductor) on swept frequency S-parameters according to an embodiment of the present application.
Figure 3:
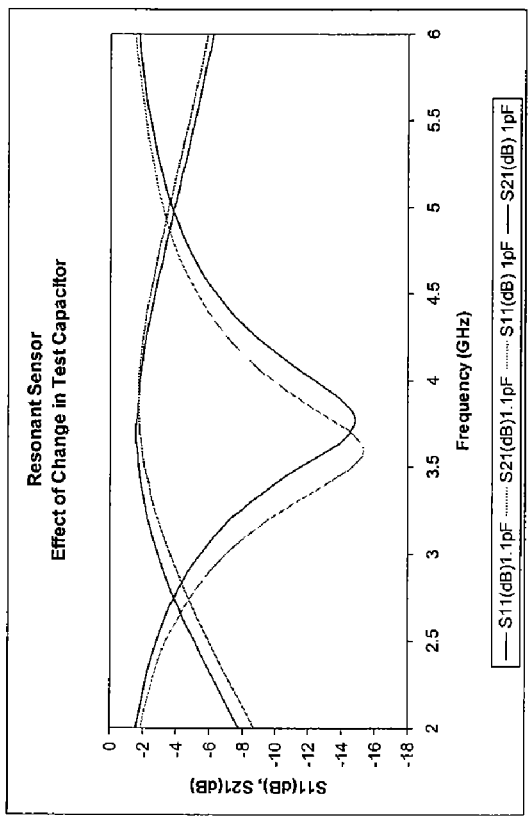
FIG. 3 graphs the resonance frequency shift due to a change in capacitance values according to an embodiment of the present application.

The above model can predict that very small changes in capacitance can result a large shift in resonance frequency. For example, it was experimentally found that a 10% change in capacitance can result in an approximate resonance frequency shift of about 200 MHz, as shown in FIG. 3. In FIG. 3, a change in resonance frequency for 10% change in test capacitor (about 1.1 pF to about 1.0 pF) can be as high as 200 MHz. Also, an increase in conductance of the polymer sensing layer 90 (which can result in the decreasing shunt resistance) can affect the amplitude of the resonance, as shown in FIG. 4. In FIG. 4, a 50% change in shunt resistance of the test capacitor can alter the amplitude of S21 by approximately 3 dB. When the shunt resistance is reduced to zero-ohms (from about 400 Ohms), the S-parameters can change significantly as shown in FIG. 5. The S21 (the ratio of output power to input power) can change by more than 12 dB, and the S11 can change by approximately 4 dB. Additionally, the change in S-parameters can be picked up in a wireless fashion as will be discussed below. The change in capacitance can also affects the phase of S21, as shown in FIG. 6. FIG. 6 shows close to 30 degrees of phase shift at 3.7 GHz. As a result, sensors can be designed with multiple measurable parameters, such as, for example, signal loss (insertion loss) in the sensor, reflected power, the amplitude of resonance, frequency of resonance, and phase of the S21.

Figure 7:
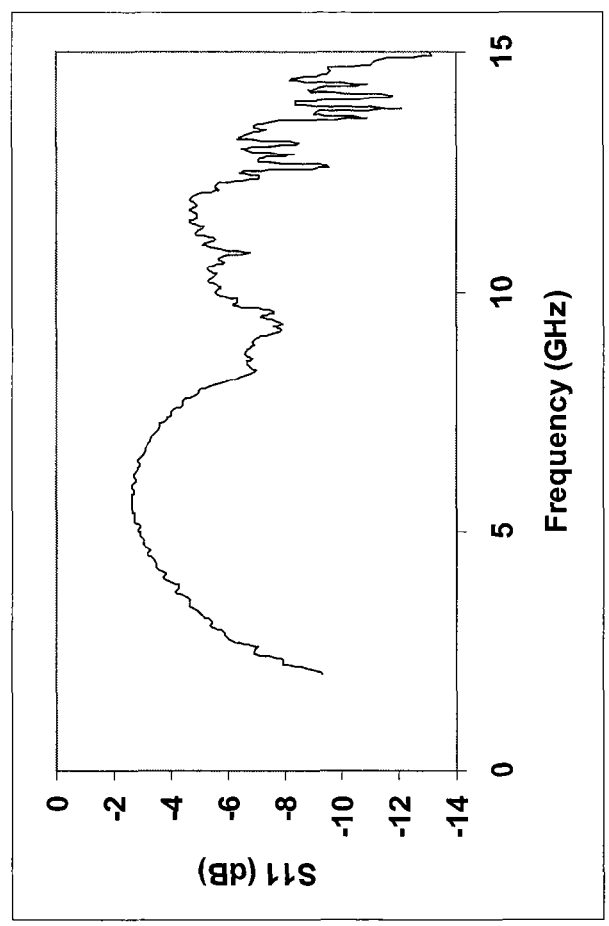
FIG. 7 graphs the experimental swept frequency scattering parameter S21 performance of a resonant sensor with a DNA-CTMA bipolymer according to an embodiment of the present application.
Figure 8:
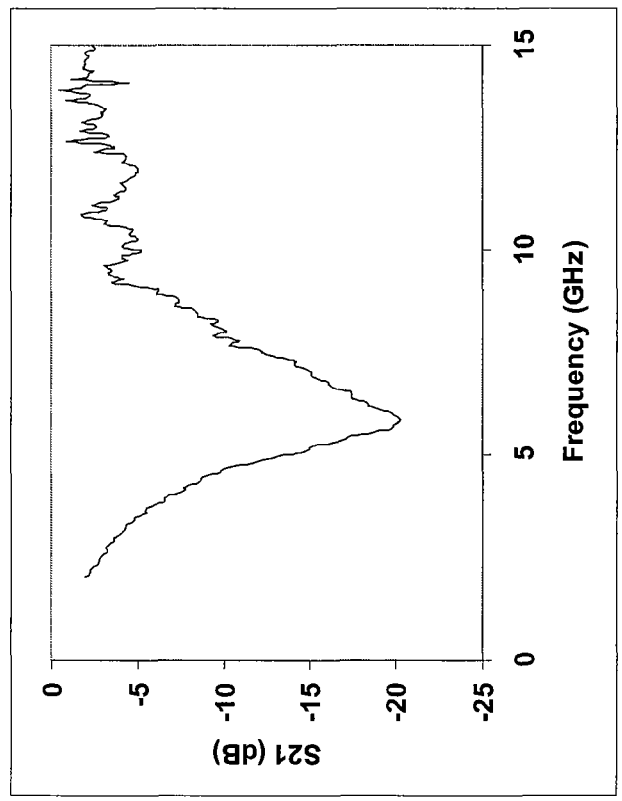
FIG. 8 graphs the experimental swept frequency scattering parameter S11 performance of the resonant sensor with a DNA-CTMA bipolymer of FIG. 7 according to an embodiment of the present application.
Figure 9:
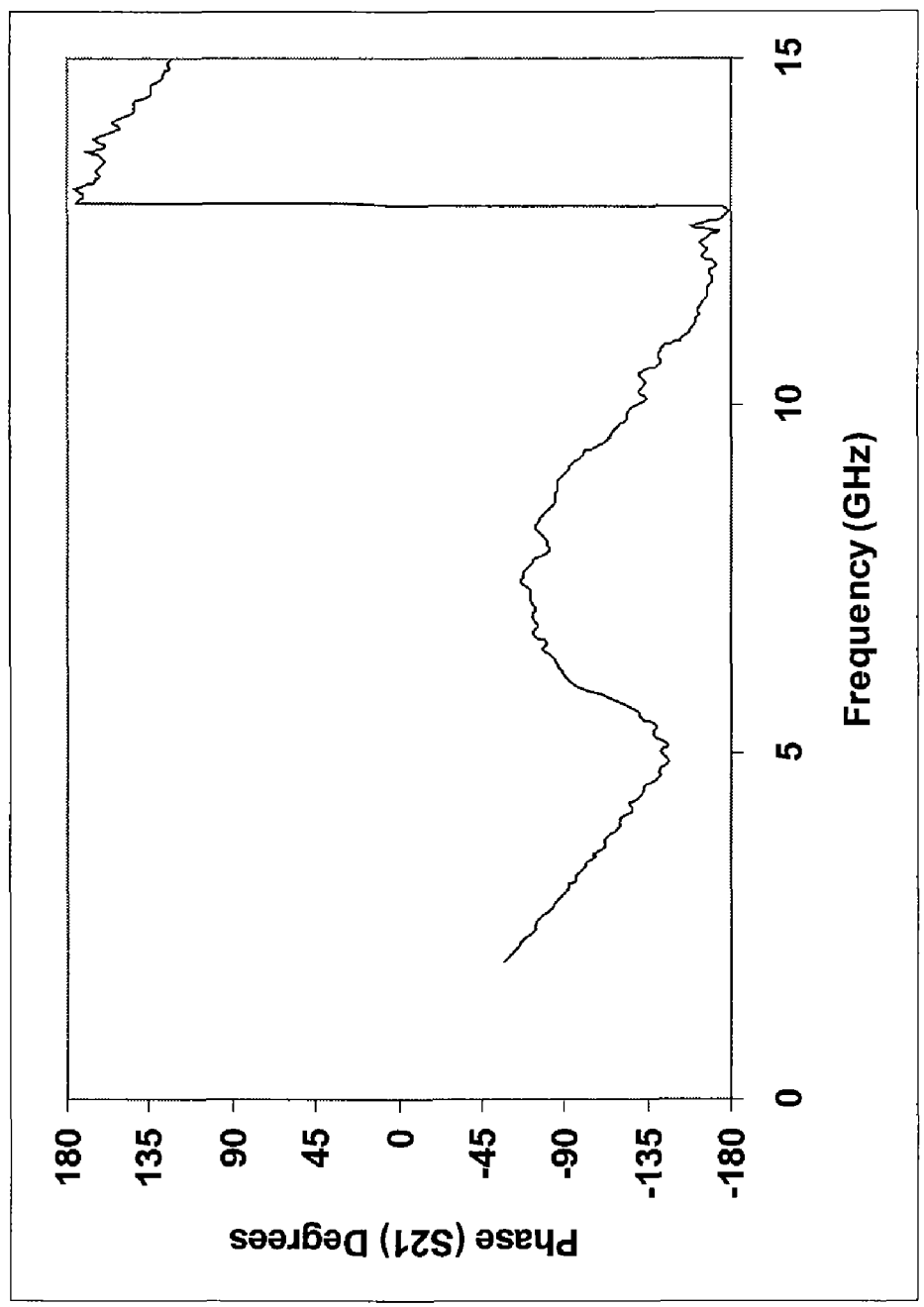
FIG. 9 graphs the insertion phase of S21 for same resonant sensor of FIG. 7 according to an embodiment of the present application.

In one embodiment, the resonant sensors can be fabricated using a DNA-CTMA biopolymer in the sensing layer 90 as discussed above. FIGS. 7-9 illustrate some of the measured S-parameters for a resonant sensor 10 with DNA-CTMA biopolymer layer 90 situated between the bottom conductive layer 40 and the top conductive layer 15. FIG. 7 shows the experimental swept frequency scattering parameter S21 (transmitted power) performance of a resonant sensor with a DNA-CTMA biopolymer, FIG. 8 graphs the swept frequency S11 (reflected power) for the same resonant sensor as in FIG. 7, and, finally, FIG. 9 graphs the insertion phase of S21 for the same resonator test structure.

As the figures indicate, there can be a distinct resonance frequency in both transmitted (S21) and reflected power (S11) as well as phase of S21 that can be detectable using the resonant test structure, and analyzing the S-parameters can give the differences between the reference sensor and the measurement sensor, potentially resulting highly sensitive, and selective resonant sensors for detecting dangerous environmental chemicals such as odors, TNT, ammonia etc. Potentially high sensitivity, higher selectivity by the use of the functionalized bipolymers and ease of wireless interrogation by measuring the reflected power from the sensor (i.e., by measuring the scattering parameter S11) can be possible.

The resonant sensor can be applicable for sensing biochemicals, trace chemicals in solid or gaseous form, as functionalized biopolymers can be used as sensing layers. The specific environmental conditions, or analytes, being sensed can result in changes in dielectric properties or electrical conductance of the sensing layer 90. The impedance changes in the device can also result in wireless passive sensing.

Additionally, the capacitive test structure used in the characterization of polymers (U.S. patent application Ser. No. 11/909,646, filed on Sep. 25, 2007, incorporated here by reference) can be easily modified to a resonant structure by adding an additional inductance in series with the capacitor as was described above.

In another embodiment, an antenna may be integrated with the resonant sensor. With the integrated antenna, passive wireless interrogation of the sensor can be possible. With antenna integration, these sensors can be truly zero-power sensors as they would not require any DC voltage or power for their operation. Additionally, each sensor can be integrated with a different frequency antenna and a continuous wave frequency modulated (CWFM) radar for wireless interrogation and sensing can be used. The sensors would be powered by the RF signal from the radar and will reflect the RF signal back to the radar. Because each sensor can be different based on impedance changes, each sensor can absorb different parts of the spectrum. In addition, a large number of sensors can be fabricated on a single chip resulting in considerable sensitivity to change in the environment.

By using an EO biopolymer as the polymer sensing layer 90 and an integrated antenna, radio frequency (RF) and EO measurement techniques can be combined to produce highly sensitive and selective nanosensors. For example, a RF signal can be used to determine the resonance frequency, amplitude of the signal loss of the sensor, or impedance changes within the sensor. Using a biopolymer with specific EO transmittance and/or absorption properties at the wavelength of the light beam used, as was discussed above, it can be determined whether a specific analyte had been captured by measuring the change in the absorption/transmission characteristics of the polymer. Since multiple RF and EO measurement parameters can be captured, highly sensitive sensors with low false-positives can be realized due to the number of measured parameters. The combined use of both RF and EO techniques can also result in increased selectivity for the sensor.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the claimed invention.

For the purposes of describing and defining the embodiments it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the embodiments in detail and by reference to specific embodiments thereof, it will be apparent that modifications and variations are possible without departing from the scope of the embodiments defined in the appended claims. More specifically, although some aspects of the embodiments are identified herein as preferred or particularly advantageous, it is contemplated that the claimed invention is not necessarily limited to these preferred aspects of the invention.

What is claimed is:

1. A resonant sensor for detecting a specific environmental analyte, the resonant sensor comprising a top conductive layer of two ground conductors and a center signal line, a bottom conductive layer of two ground lines shunted together by a shunt line and a sensing layer positioned between the top conductive layer and the bottom conductive layer, wherein:
   the shunt line has a non-linear pattern adding inductance to the shunt line;
   a capacitive area is created by the overlap of the center signal line of the top conductive layer and the shunt line of the bottom conductive layer; and
   a change in electrical properties of the sensing layer in response to binding of the specific environmental analyte with the sensing layer produces a corresponding change in capacitance or leakage conductance between the top conductive layer and the bottom conductive layer or between the center signal line and the ground line, the corresponding change indicating the detection of the specific environmental analyte.

2. The resonant sensor of claim 1, wherein the shunt line and the capacitive area form an electrical circuit with a resonant frequency.

3. The resonant sensor of claim 1, wherein the sensing layer comprises an electro-optic polymer.

4. The resonant sensor of claim 3, wherein the electro-optic polymer is DNA-CTMA or BSA.

5. The resonant sensor of claim 1, wherein the sensing layer comprises a piezoelectric thin film.

6. The resonant sensor of claim 1, wherein the sensing layer comprises a three layer optical waveguide structure.

7. The resonant sensor of claim 1, wherein the specific environmental analyte is chemical, biochemical, biological or combinations thereof.

8. The resonant sensor of claim 1, wherein the specific environmental analyte is in gaseous or solid phase.

9. The resonant sensor of claim 1, wherein the specific environmental analyte is TNT or ammonia.

10. The resonant sensor of claim 1, wherein the resonant sensor is fabricated on a substrate.

11. The resonant sensor of claim 10, wherein the substrate comprises silicon, sapphire, alumina, plastic or glass.

12. The resonant sensor of claim 1, wherein the top conductive layer is perforated.

13. The resonant sensor of claim 1, wherein the top conductive layer and the bottom conductive layer comprise metal, conductive polymers, or combinations thereof.

14. The resonant sensor of claim 1, further comprising, an integrated antenna.

15. A resonant sensor for detecting a specific environmental analyte, the resonant sensor comprising a top conductive layer of two ground conductors and a center signal line, a bottom conductive layer of two ground lines shunted together by a shunt line and an electro-optic polymer sensing layer positioned between the top conductive layer and the bottom conductive layer, wherein:
   the shunt line has a non-linear pattern adding inductance to the shunt line;
   the electro-optic polymer sensing layer comprises gold nanoparticles embedded in the electro-optic polymer sensing layer;
   a capacitive area is created by the overlap of the center signal line of the top conductive layer and the shunt line of the bottom conductive layer; and
   a change in electrical properties of the electro-optic polymer sensing layer in response to binding of the specific environmental analyte with the gold nanoparticles embedded within the electro-optic polymer sensing layer produces a corresponding change in capacitance or leakage conductance between the top conductive layer and the bottom conductive layer or between the center signal line and the ground line, the corresponding change indicating the detection of the specific environmental analyte.

16. The resonant sensor of claim 15, wherein the electro-optic polymer sensing layer comprises DNA-CTMA or BSA.

17. The resonant sensor of claim 16, wherein the specific environmental analyte is TNT or ammonia.

* * * * *